US008543187B2

(12) United States Patent
Miyazaki (10) Patent No.: US 8,543,187 B2
(45) Date of Patent: Sep. 24, 2013

(54) NON-CONTRAST MRI SIGNAL ACQUISITION

(75) Inventor: Mitsue Miyazaki, Mount Prospect, IL (US)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 341 days.

(21) Appl. No.: 12/923,892

(22) Filed: Oct. 13, 2010

(65) Prior Publication Data

US 2012/0095327 A1    Apr. 19, 2012

(51) Int. Cl.
*A61B 5/05*    (2006.01)

(52) U.S. Cl.
USPC ........... 600/410; 600/413; 600/416; 600/417; 600/419

(58) Field of Classification Search
USPC .......................................... 600/407, 410–423
See application file for complete search history.

(56) References Cited

U.S. PATENT DOCUMENTS

| 5,054,489 | A  | * | 10/1991 | Axel et al. ................... 600/419 |
| 6,192,264 | B1 | * | 2/2001 | Foo et al. ..................... 600/413 |
| 2002/0060566 | A1 | * | 5/2002 | Debbins et al. ............... 324/307 |
| 2004/0155653 | A1 | * | 8/2004 | Larson et al. ................. 324/309 |
| 2008/0009705 | A1 |   | 1/2008 | Furudate |
| 2009/0005670 | A1 |   | 1/2009 | Ichinose et al. |
| 2009/0149734 | A1 |   | 6/2009 | Sugiura |
| 2010/0249574 | A1 |   | 9/2010 | Miyazaki |

FOREIGN PATENT DOCUMENTS

| JP | 2006-158512 | 6/2006 |
| JP | 2008-23317 A | 2/2008 |
| JP | 2009-028525 | 2/2009 |
| JP | 2009-153965 | 7/2009 |
| WO | 88/07349 | 10/1988 |

OTHER PUBLICATIONS

Kanazawa et al. "Time-Spatial Labeling Inversion Tag (t-SLIT) using a Selective IR-Tag On/Off Pulse in 2D and 3D half-Fourier FSE as Arterial Spin Labeling" Proc. Intl. Soc. Mag. Reson. Med. 10, 2002, p. 1.*

Miyazaki, et al., "Non-contrast-enhanced MR angiography using 3D ECG-synchronized half-Fourier fast spin echo," *JMRI* 12:776-783 (2000).

Furudate, et al., "FBI-Navi for Easy Determination of Diastolic and Systolic Triggering Phases in Non-Contrast Fresh Blood Imaging (FBI)," ISMRM 16th Annual Meeting, Toronto, p. 2902 (2008).

(Continued)

*Primary Examiner* — James Kish
(74) *Attorney, Agent, or Firm* — Nixon & Vanderhye PC (57) ABSTRACT

A first plurality of MR signals from a patient's tissue at respectively corresponding successive first time increments extending over a first time interval including a substantial majority of a subject's cardiac cycle is acquired and analyzed to define a second time interval, shorter than the first time interval, during the cardiac cycle whereat there is a relatively steep rise in signal magnitudes as a function of time (e.g., corresponding with systole and diastole events of the cardiac cycle). A second plurality of MR signals is then acquired from tissue of the patient at respectively corresponding successive second time increments during the second time interval, the second time increments being substantially shorter than said first time increments. Image data representing at least one contrast-free image of flowing fluid vessels is generated based on the second plurality of MR signals.

26 Claims, 7 Drawing Sheets

(56) References Cited

OTHER PUBLICATIONS

Miyazaki, et al., "Peripheral MR angiography: Separation of Arteries from Veins with Flow-spoiled Gradient Pulses in Electrocardiography-triggered Three-dimensional Half-Fourier Fast Spin-Echo Imaging," *Radiology* 227:890-896 (2003).

Nakamura, et al., "Flow-Motion FBI, a novel non-contrast-enhanced 3D-MRDSA technique using ECG-Triggered Three-Dimensional Half-Fourier FSE—the feasibility to evaluate hemodynamics of peripheral vascular diseases," Proc. Intl. Soc. *Mag. Reson. Med*. 13, p. 1713 (2005).

Nakamura, et al., "Feasibility of quantitative analysis of non-contrast-enhanced MRDSA using ECG-gated two-dimensional half-Fourier FSE for the assessment of peripheral vascular diseases," Proc. Intl. Soc. *Mag. Reson. Med. 14*, presented at the ISMRM 14th Annual Meeting, Seattle, Washington, p. 1933 (2006).

International Search Report mailed Dec. 20, 2011 in PCT/JP2011/073569.

A. M. Gharib et al., "Coronary MR Angiography at 3T During Diastole and Systole," Proc. Intl. Soc. Mag. Reson. Med. 14, May 2006, p. 2164.

P. Lai et al., "Respiratory Self-gated 4D Coronary MRA," Proc. Intl. Soc. Mag. Reson. Med. 14, May 2006, p. 364.

X. Bi et al., "A fully automated selection of the optimal data acquisition window in coronary MRA eliminating the need for user-interaction," Proc. Intl. Soc. Mag. Reson. Med. 15, May 2007, p. 2488.

M. M. Fung et al., "Multi-phase Fat-Suppressed 3D SSFP for Robust Coronary Artery Imaging: Improvements over the single phase technique," Proc. Intl. Soc. Mag. Reson. Med. 16, May 2008, p. 313.

Mitsue Miyazaki et al., "Nonenhanced MR Angiography," Radiology, Jul. 2008, vol. 248, No. 1, pp. 20-43.

\* cited by examiner

NON-CONTRAST MRI SIGNAL ACQUISITION

FIELD

The subject matter below relates generally to magnetic resonance imaging (MRI) processes. More particularly, MRI data acquisition techniques are described that enable more efficient acquisition of MRI data useful, e.g., in creating time-resolved non-contrast MR images.

DETAILED DESCRIPTION

Figure 1:
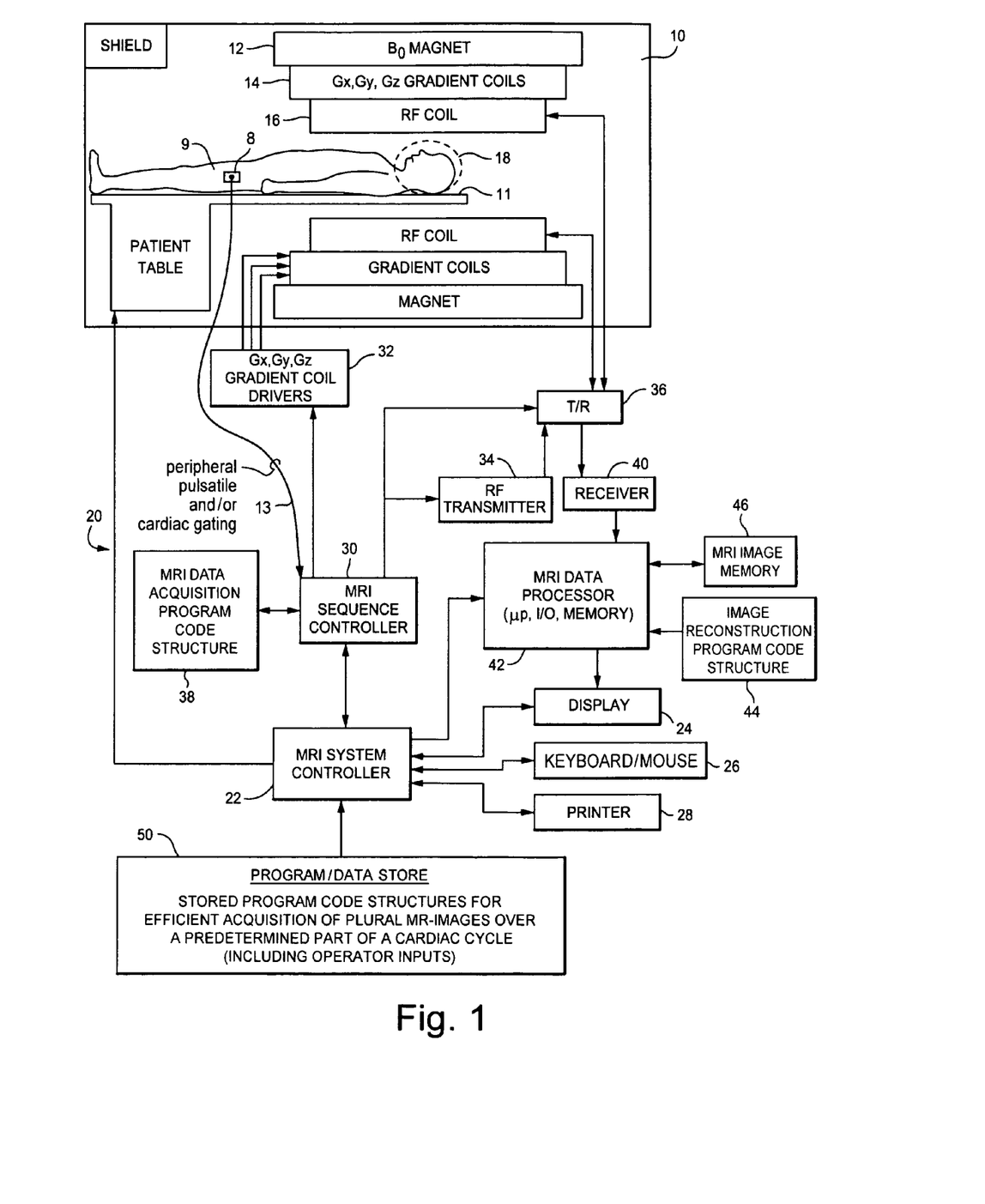
FIG. 1 is a high-level schematic block diagram of an MRI system adapted to acquire and process data for MRA (magnetic resonance angiography) using magnetic resonance data based on plural images acquired at different times within a cardiac cycle.

The MRI system shown in FIG. 1 includes a gantry 10 (shown in schematic cross-section) and various related system components 20 interfaced therewith. At least the gantry 10 is typically located in a shielded room. One MRI system geometry depicted in FIG. 1 includes a substantially coaxial cylindrical arrangement of the static field BO magnet 12, a $G_x$, $G_y$, and $G_z$ gradient coil set 14 and an RF coil assembly 16. Along the horizontal axis of this cylindrical array of elements is an imaging volume 18 shown as substantially encompassing the head of a patient 9 supported by a patient table 11.

An MRI system controller 22 has input/output ports connected to display 24, keyboard/mouse 26 and printer 28. As will be appreciated, the display 24 may be of the touch-screen variety so that it provides control inputs as well.

The MRI system controller 22 interfaces with MRI sequence controller 30 which, in turn, controls the $G_x$, $G_y$ and $G_z$ gradient coil drivers 32, as well as the RF transmitter 34 and the transmit/receive switch 36 (if the same RF coil is used for both transmission and reception). The MRI sequence controller 30 includes suitable program code structure 38 for implementing MRI data acquisition sequences available in the repertoire of the MRI sequence controller 30. Cardiac signal acquisition apparatus 8 (positioned as appropriate on the patient anatomy) may be used to provide peripheral pulsatile and/or cardiac gating signals 13 to trigger the MRI sequence controller 30.

The MRI system 20 includes an RF receiver 40 providing input to data processor 42 so as to create processed image data to display 24. The MRI data processor 42 is also configured for access to image reconstruction program code structure 44 and to MR image memory 46 (e.g., for storing MR image data derived from processing in accordance with the exemplary embodiments and the image reconstruction program code structure 44).

Also illustrated in FIG. 1 is a generalized depiction of an MRI system program/data store 50 where stored program code structures (e.g., for image reconstruction such as non-contrast MRA and pre-scan systole/diastole determinations within a cardiac cycle, operator inputs to same, etc.) are stored in computer-readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those in the art will appreciate, the FIG. 1 depiction is a very high-level simplified diagram of a typical MRI system with some modifications so as to practice exemplary embodiments to be described hereinbelow. The system components can be divided into different logical collections of "boxes" and typically comprise numerous digital signal processors (DSP), microprocessors, special purpose processing circuits (e.g., for fast ND conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an MR-imaging reconstruction process, an array of computer-readable accessible data value storage sites in physical storage media will be transformed from some prior state (e.g., all uniform "zero" values or all "one" values) to a new state wherein the physical states at the physical sites of such an array vary between minimum and maximum values to represent real world physical events and conditions (e.g., the blood flowing in arteries of a patient over an imaging volume space). As those in the art will appreciate, such arrays of stored data values represent and also constitute a physical structure—as does a particular structure of computer control program codes that, when sequentially loaded into instruction registers and executed by one or more CPUs of the MRI system 20, cause a particular sequence of operational states to occur and be transitioned through within the MRI system.

The exemplary embodiments described below provide improved ways to process data acquisitions and/or to generate and display MR-images.

Time resolved non-contrast MRA (magnetic resonance angiography) can be obtained by successively acquiring MR images at small incremental delay (repeat) times throughout an R-R cycle so as to surely include system to diastole and the subtraction of dark signals at systole from the bright signals at or during diastole. This provides one or more images of blood travel between systole to diastole times in the cardiac cycle.

However, since one does not initially know where the appropriate sub-period or sub-interval of a cardiac cycle resides in the PQRSTU complex, all data is acquired with small increments of delay to acquire finely separated data acquisition sequences over a whole cardiac R-R period and then find the most suitable images at (a) diastole and (b) systole to subtract and produce the desired time-resolved fluid vascular (e.g., MRA) image.

To reduce wasted resource usage, the exemplary embodiment first performs an ECG-Prep rough scan with relatively large rough increments (e.g., like 100 ms) to cover a whole cardiac cycle. FBI-Navi or some similar program can be used to display a graph of the rough scan signal intensity versus delay time to allow operator selection of the beginning and the end of steep signal changes—and a finer final imaging increment that can be operator selected. The exemplary system can also automatically calculate the final scan repeat interval (i.e., how many times to repeat a scan within the defined interval). For example, an Auto-ECG mode as described in co-pending commonly assigned application 12/699,169 may be employed to use the heart rate to calculate systolic and diastolic periods and to determine systolic and diastolic triggering delays.

The signals from the "black" systole image are automatically subtracted from the bright diastolic signals, or vice versa, to display time-resolved images (2D and 3D). In cine mode, a sequence of such images can show flow-like hemodynamic images. Similarly, in time-SLIP time-resolved images, a 2D BBTI-Prep scan can display an FBI-Navi-like plot of BBTI-prep results and an operator may select a desired period and/or repeat parameters for the data acquisition in 2D and/or 3D.

Time-resolved non-contrast images can be obtained using FBI-Navi-aided selection of signal acquisition duration during a relevant signal changing area (which alternatively can be automatically system selected to encompass detected steep slope periods instead of relying upon an operator's selection).

An exemplary GUI of the above interface and system scan operation and subtraction can produce flow-like images while allowing a reduction of scan time to obtain time-resolved non-contrast images in FBI and time-SLIP sequences.

Because one does not initially know when particular signal intensity changes occur within a cardiac cycle, multiple scans with a small increment (for example, 10 msec) have been used to cover a whole cardiac cycle, such as an R-R interval of 1,000 ms where using an increment of 10 ms would require 100 MRI data acquisition sequences. Using a 3RR interval per scan, 2D scan to make a 3D scan (2D spatial data with 1D in time) will take 3RR×100=300RRs or 300 cardiac beats. 300×1000 ms=300 sec or 5 minutes. For sufficient 3D scans to collect 4D data (3D spatial data with 1D in time), it may thus take 50 minutes for 10 slices. In addition, the post-acquisition processing of those extensive acquired data sets takes a long time (e.g., due to not initially knowing where the diastolic or high signal intensity is to be found for subtraction and where the lowest or peak systolic phase may be located).

Figure 2:
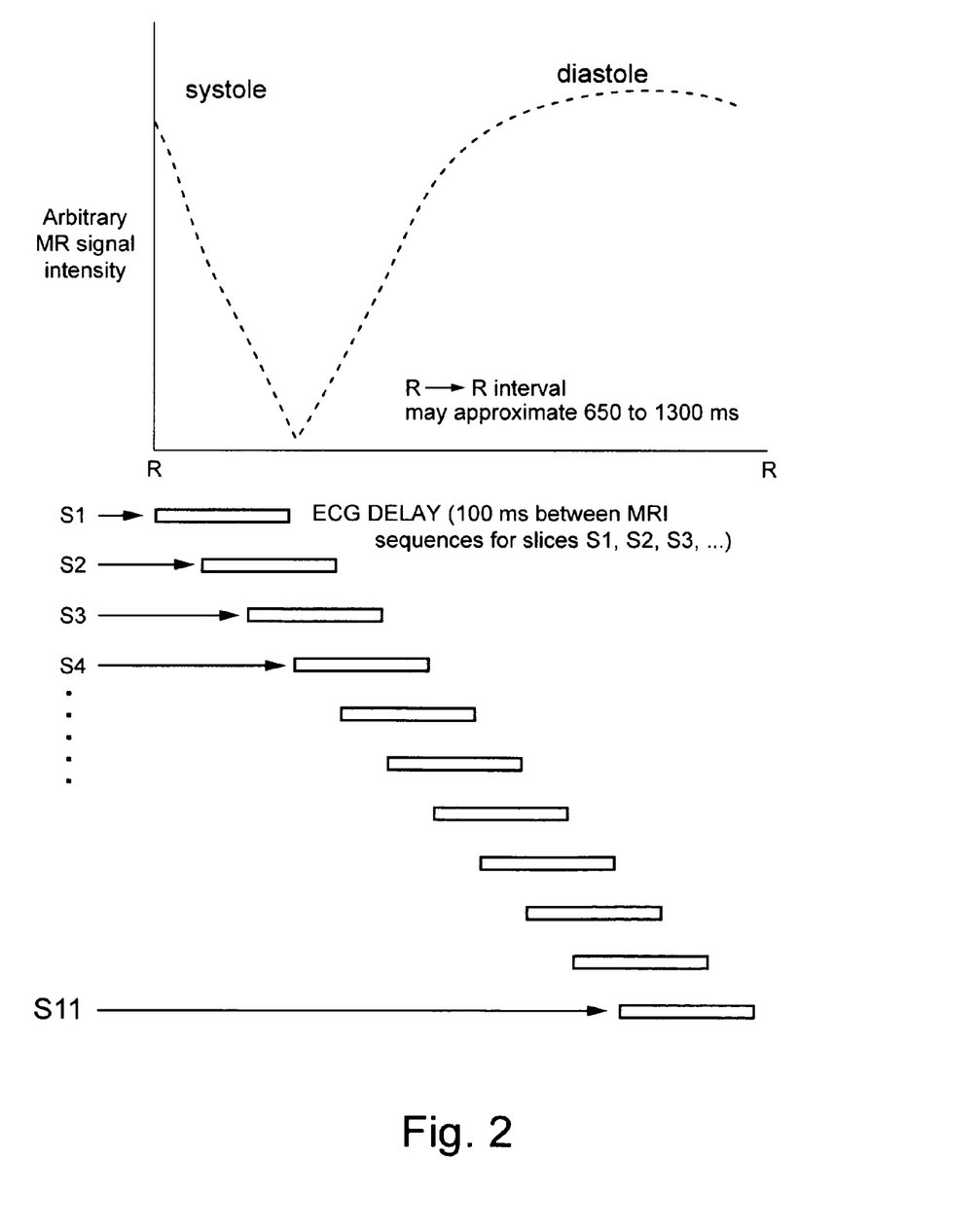
FIG. 2 is a schematic diagram showing MR signal intensity versus time over a cardiac R-R interval as measured roughly by a succession of successively delayed MRI slice imaging sequences in an exemplary embodiment so as to quickly identify a desired sub-interval (e.g., a systole/diastole interval)
Figure 3:
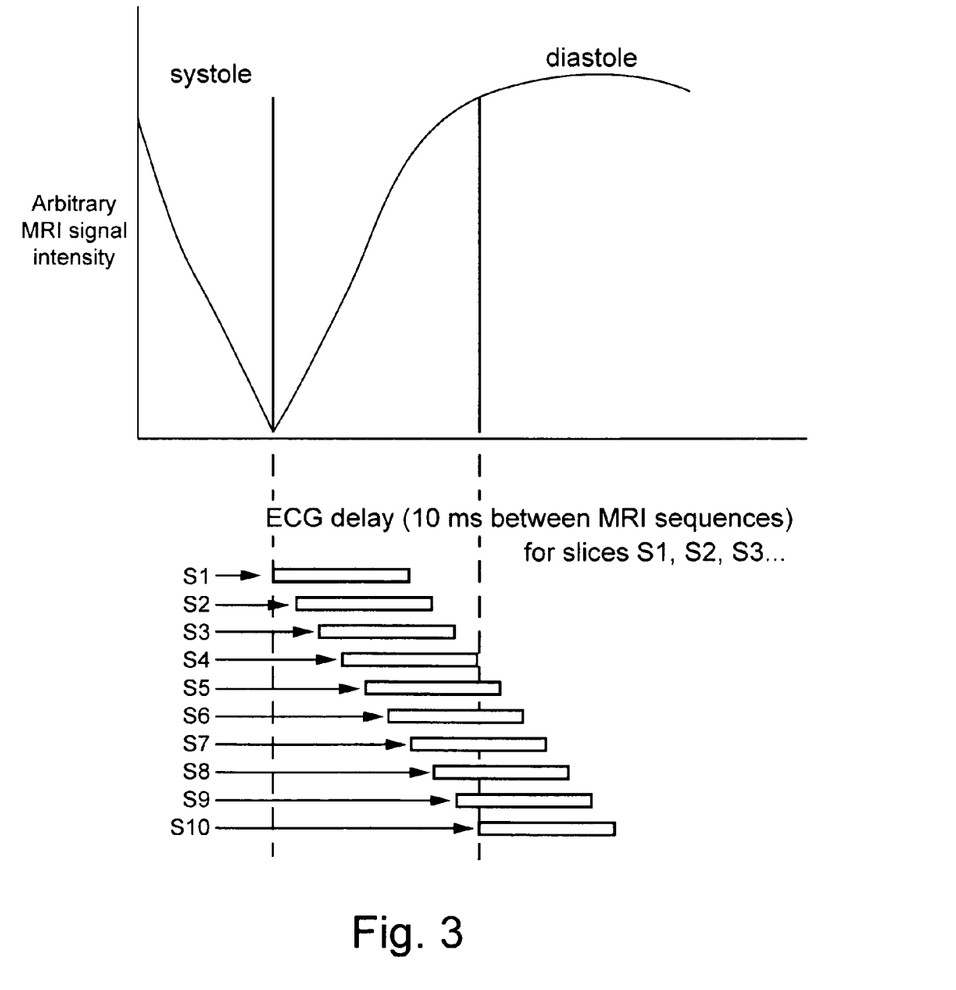
FIG. 3 is similar to FIG. 2, but now accomplished using a fewer number but more closely spaced (in time) slice imaging sequences taken within the shorter systole/diastole interval identified using the rough scan of FIG. 2.
Figure 5:
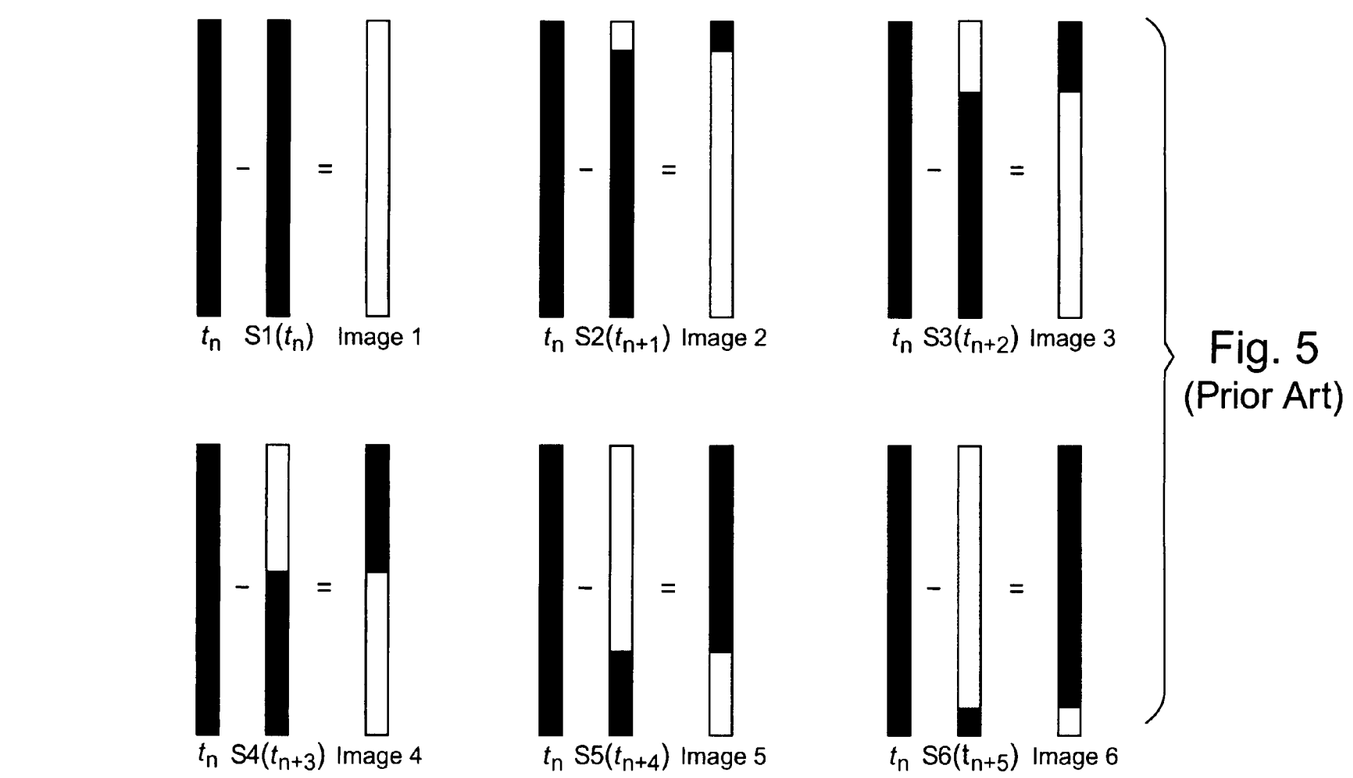
FIG. 5 is a schematic diagram of a succession of difference images that can be obtained by subtracting a "dark" base systole image and each of a succession of "brighter" images on a pixel-by-pixel basis as the MRI data acquisition sequence is moved towards diastole.
Figure 6:
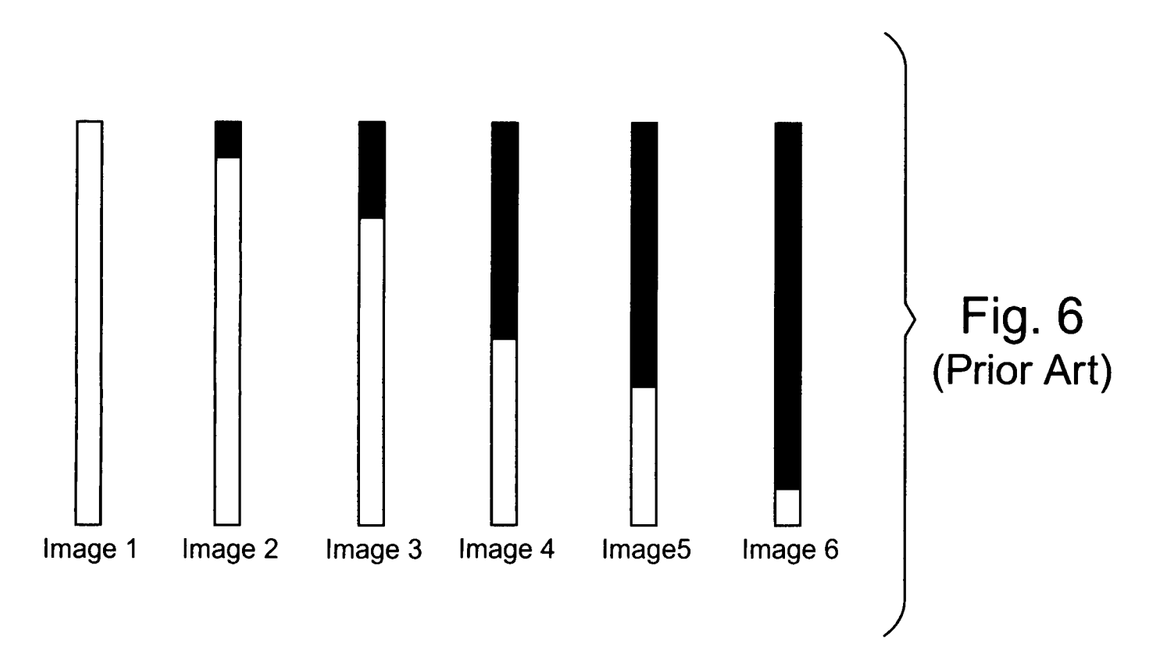
FIG. 6 is an extract showing images 1-6 derived from FIG. 5.

As noted above, typically, due to not knowing the signal intensity curve for a particular patient in advance, a whole cardiac cycle of consecutively delayed slice images was acquired using single shot FSE (FASE) or any other suitable MRA sequences (EPI, bSSFP, etc.) with a small increment like 10-20 msec. Now, however, in order to initially ascertain a rough signal intensity curve, an ECG-prep scan using a relatively large increment (roughly like 100 ms) can be used to cover a whole cardiac cycle, as shown in FIG. 2. By using an FBI-Navi (a plot of signal intensity versus ECG time), one can select start and end scan times and a desired shorter increment for the consecutively delayed MRI sequences as shown in FIG. 3. Subtraction of lower intensity signals in systole from higher intensity signals at diastolic triggered images will give time-resolved MRA images visually representing moving blood signals, as shown in FIG. 5, where S1, S2, . . . Sn are systolic phases 1, 2, . . . n. If displayed in cine mode (FIG. 6), non-contrast time-resolved MRA can be seen.

Acquiring only the steep signal change from systolic to diastolic with the smaller delay increment allows an overall faster scan time for time-resolved non-contrast MRA. Further shortening of scan time can be made using:

- T2 plus (90 degree flip back pulse at the end of the acquisition to bring the x-y magnetization to the +z direction)
- Higher parallel imaging factor to shorten an actual single shot time and reducing the TR from 3RR interval to 1 or 2RR interval
- A keyhole type scan to share the peripheral k-space data using a full sample at the diastole (or systole) and a center part of k-space to acquire and share the non-acquired part (elsewhere than a center) to make images.

This provides shorter scan time to obtain a non-contrast time-resolved in 2D spatial with 1D time images or 3D spatial with 1D time images. An easy to use GUI can be provided for this time-resolved technique using the systolic to diastolic period by selecting the start and end of the scan period and by presetting the delay increment (e.g., by having the system calculate a repeat increment).

Non-contrast time-resolved images (2D spatial+1D time=3D or 3D+1D time=4D) imaging can be obtained using this type of ECG-Prep or FBI-Navi result. Without this approach, one acquired a single shot FSE image at a small repeat increment over the whole cardiac cycle, which takes a long time Now, one can use the result of the initial rough FBI-Navi to select the start and end time(s) of scan(s) and, if desired, a delay increment to cover the low intensity signal (systolic) to high intensity signal (diastolic) triggering times. The system may automatically calculate the repeat interval and acquire multiple scans in different phases (2D or 3D scans) and subtract the systolic data from diastolic data (or vice versa) to display time-resolved MR images as flow dynamics.

This approach can provide time-resolved non-contrast images obtained using FBI-Navi, selection of duration (signal change area, which can be automatically system selected (steep slope detection) or operator selected). A friendly GUI of the above interface and system scan operation and subtraction can produce flow-like images.

In the exemplary embodiments, since the MR signal intensity versus time curve throughout an R-R interval of the cardiac cycle for a particular patient is not known in advance, a rough scan of the interval for a given patient may be utilized to quickly discern the location of systole and diastole timings. For example, as shown in FIG. 2, a succession of MRI slice imaging sequences S1, S2 . . . may be effected at relatively large intervals (e.g., 100 or so msec) over the R-R interval for that patient (which may approximate 650 to 1,300 msec or so). In this manner, the MR signal intensity over the R-R interval is initially mapped out as depicted in FIG. 2 so as to identify the timing of minimum MR signal intensity (systole) and the timing of maximum MR signal intensity (diastole).

Once the systole and diastole time points have been identified for that particular patient, then a more concentrated (i.e., more closely spaced in time series of successively delayed MRI slice imaging sequences may be effected so as to capture the most desirable part of the R-R cycle, namely, between systole and diastole as depicted in FIG. 3. Here, the MRI sequences may be more closely spaced (e.g., 10 msec or so) so as to provide the desired level of incremental change between images. This allows the use of techniques such as FBI (fresh blood imaging)-Navi in 2D and/or 3D acquisitions as time-resolved non-contrast MRA images. When these successive images are displayed in cine mode, they appear as a hemodynamic display of blood flowing through vessels (or other fluids flowing through other appropriate vessels) within the imaged patient body part. However, by first doing an initial rough scan as in FIG. 2 in order to map out the MR signal intensity curve during an R-R interval for a given patient and then concentrating only on the desired (e.g., systole/diastole) part of that curve for the more finely closely separated series of images, one can effectively save a considerable amount of time.

Figure 4:
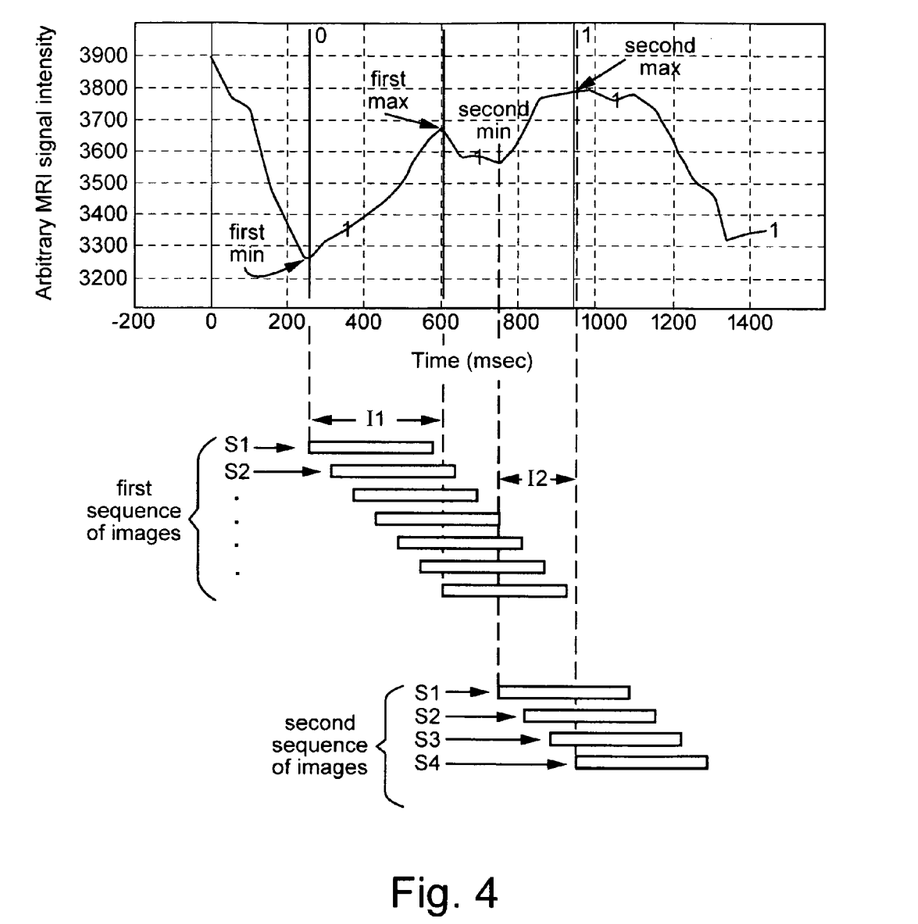
FIG. 4 is similar to FIG. 3, but illustrates the possibility of capturing a plurality of relevant positively-sloped signal intervals that may be separated from one another within the systole/diastole interval.

As depicted in FIG. 4, some patients may have an MR signal intensity curve that has more than one pair of minimum and maximum points. As shown in FIG. 4, for example, first minimum and first maximum systole/diastole points define a first interval I1 that captures most of the positively sloped intensity curve for which a first sequence of images is then captured. However, in addition, this particular patient exhibits a second interval I2 with a second minimum and a second maximum. Accordingly, this second smaller interval defining a second smaller positively sloped region can also be captured in a second sequence of consecutively delayed slice imaging MRI sequences as also depicted in FIG. 4. In effect, this permits the capturing of positively sloped portions of the intensity curve that occur in later time segments.

FIG. 5 schematically depicts idealized sections of a linear artery that has been imaged at various timings and then subtracted (e.g., diastolic-systolic) to produce a series of images that can be displayed in cine mode (e.g., see FIG. 6) to simulate a hemodynamic video display showing an advancing volume of blood through that imaged section of artery. While this type of FBI-Navi display is, of course, known in the prior art, the use of an initial rough, longer interval, mapping sequence as in FIG. 2 so as to permit restriction of the closer spaced successive images more precisely in a thusly identified systole/diastole interval as shown in FIGS. 3 and 4 greatly decreases the overall data acquisition time.

Changes in arterial signal intensity can be drastic from end systolic to early diastolic. However, each patient has a different timing for this change. In order to find the most relevant time period when there is increasing signal intensity, FBI-Navi can be used to determine a rough estimation of systolic and diastolic triggering times (e.g., as acquired using an ECG-Prep scan, single slice with multiple phases).

In order to reduce total acquisition time for time-resolved non-contrast MRA, using the result of the prep-scan FBI-Navi, time-resolved images can be more efficiently acquired in the period of drastically increasing signal change from late systole to early diastole.

To efficiently obtain time-resolved non-contrast MRA images, a drastically increasing signal change period from late systole to early diastole can be automatically determined using the FBI-Navi, as shown in FIG. 2. Thereafter, the system can automatically determine the optimum scan period. An operator can selectively determine the incremental delay and/or the system can calculate a suitable repeat time to acquire successively delayed slice images throughout the systole to diastole period. The system may then subtract each of the successive systolic images from the diastolic triggered image (high intensity signal) and can display the succession of subtracted images.

The desired signal change period (e.g., late systole to early diastole) as measured using pre-scan FBI-Navi can then be acquired with a smaller delay increment—or a signal change period calculated by Auto-ECG (e.g., see co-pending application Ser. No. 12/699,169) can be used with a smaller increment. Auto-ECG uses heart rate and the measured systolic and diastolic period to calculate a suitable delay interval. Auto-ECG can also automatically determine systolic and diastolic triggering delays.

The system also may automatically determine only the systole/diastole period and let the operator decide upon a desired incremental delay or suggested increment (e.g., 10-20 ms). The system may then calculate an appropriate repeat time to acquire successive images through the relevant period. The system then subtracts the systolic images from the diastolic triggered image (high intensity signal) and displays the subtracted images.

Auto-ECG may use heart rate and the systolic and diastolic period to determine systolic and diastolic triggering delays.

Time-resolved non-contrast MRA data can thus be acquired in a shorter time. The acquisition period can be selected in an easier manner and data processing (e.g., subtraction), which is cumbersome to do manually, can be done in the system. The system display can be done without manual display in a cine mode.

Figure 7:
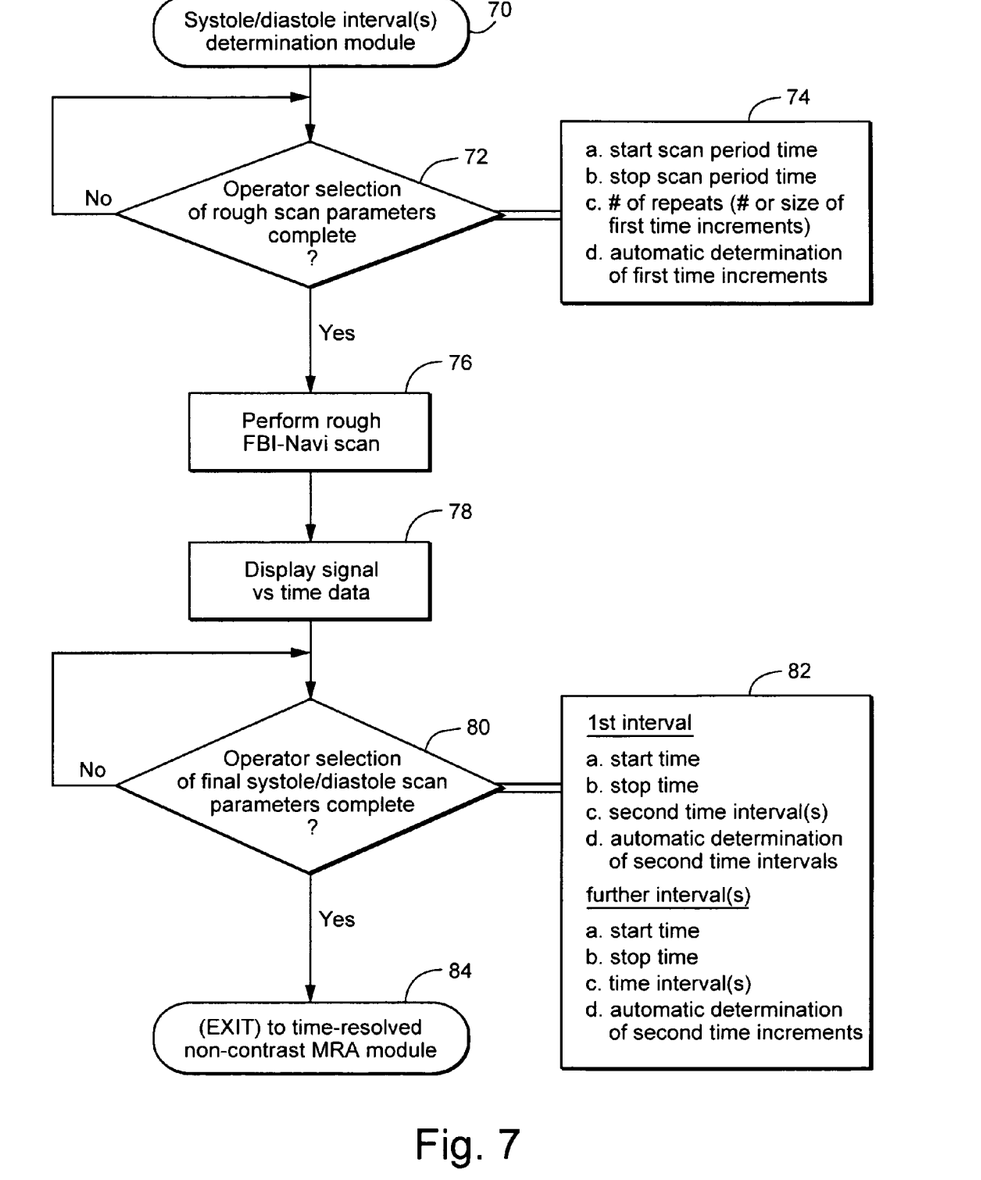
FIG. 7 is a schematic flow chart of exemplary computer program code structure that may be utilized for practicing an exemplary embodiment.

Exemplary program code structure for a systole/diastole interval determination module is depicted at FIG. 7. There, the module is entered at 70 (e.g., via a suitable operator and/or system command associated with a desire to acquire/display time-resolved MRA images). At 72, a wait loop is entered for operator selection of rough scan parameters. Such operator selections may encompass, for example, items such as shown in box 74 where the operator may define start and stop scan period times (e.g., R-R interval), the number of repeats or size of delay time increments or the like (or may opt to simply let the system automatically determine these first rough scan parameters). Once operator inputs are completed, then a rough FBI-Navi scan is performed at 76. If further operator inputs are to be permitted (i.e., if fully automatic system operation is not desired), then the resulting rough scan signal versus time data may be displayed at 78 before entering a wait loop at 80 for operator selection of the final systole/diastole scan parameters. As depicted in box 82, such operator selections may include selections for more than one interval. However, for at least the first interval, the operator may enter start and stop scan times, as well as second smaller time intervals—or may merely opt to let the system automatically determine suitable smaller time intervals for the subsequent time-resolved MRA scanning process.

Once final operator inputs have been completed, then control is passed to 84 for time-resolved non-contrast MRA processes conducted in accordance with those operator-set parameters (e.g., as may be accomplished by exit to a separate module where conventional time-resolved non-contrast MRA is performed within the more limited systole/diastole time interval(s) as determined by the rough scan processes described in the earlier portions of FIG. 7.

Of course, those in the art will appreciate that, if desired, substantially all of the processes set forth in FIG. 7 could be programmed for automatic implementation by the system without repeated operator control inputs. For example, the operator inputs, if any, could be limited to the pre-setting of preference parameters or the like in an overall module for time-resolved non-contrast MRA.

While certain embodiments of the inventions have been described, these embodiments have been presented by way of example only, and are not intended to limit the scope of the inventions. Indeed, the novel methods and systems described herein may be embodied in a variety of other forms. Furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A computer-implemented method for acquiring a plurality of MR-images at respectively corresponding times related to a subject's cardiac cycle, said method comprising use of an MRI system having at least one programmed computer to:
   acquire a first plurality of MR signals from a patient's tissue at respectively corresponding successive first time increments extending over a first time interval including a substantial majority of a subject's cardiac cycle;
   analyze data representing magnitudes of the acquired first plurality of MR signals to define a second time interval, shorter than said first time interval, during the cardiac cycle whereat there is a relatively steep rise in signal magnitudes as a function of time corresponding with systole and diastole events of the cardiac cycle;
   acquire a second plurality of MR signals from tissue of said patient at respectively corresponding successive second time increments during said second time interval, said second time increments being substantially shorter than said first time increments;
   generate image data representing at least one contrast-free image of flowing fluid vessels based on said second plurality of MR signals respectively acquired at different times during said second time interval; and
   output said generated image data to at least one of: (a) a display, (b) a non-transitory data storage medium, and (c) a remote device.

2. A computer-implemented method as in claim 1, wherein said data representing magnitudes of the acquired first plurality of MR signals is displayed to an operator and an operator control input is accepted to define said second time interval based on such displayed data.

3. A computer-implemented method as in claim 2, wherein said second time increment is automatically determined by the programmed computer based on said operator-defined time interval.

4. A computer-implemented method as in claim 1, wherein said data representing magnitudes of the acquired first plurality of MR signals is automatically analyzed by said programmed computer and said second time interval is automatically defined by said programmed computer based on such data.

5. A computer-implemented method as in claim 1, wherein said first time increments are on the order of 100 ms and said second time increments are on the order of 10 ms.

6. A computer-implemented method as in claim 1, wherein said first time interval is triggered to begin by the occurrence of an R-peak in a QRS cardiac cycle.

7. A computer-implemented method as in claim 1, wherein an image subtraction process is implemented to produce an image of flowing fluid vessels and the second time interval defines a time interval between systole and diastole of a cardiac cycle.

8. A computer-implemented method as in claim 7, wherein successive difference images are generated between an MR-image acquired at systole and successive MR-images acquired at times approaching and/or at diastole.

9. A computer-implemented method as in claim 8, wherein said successive difference images are displayed in cine mode to display flow-like hemodynamic images.

10. A computer-implemented method as in claim 7, wherein said image of flowing fluid vessels is a 2D image.

11. A computer-implemented method as in claim 7, wherein said image of flowing fluid vessels is a 3D image.

12. A computer-implemented method as in claim 1, wherein a time-SLIP (spatial labeling inversion pulse) process is implemented to produce a contrast-free MR-image of flowing fluid vessels.

13. A computer-implemented method as in claim 1, wherein a 2D BBTI (black-blood time to inversion) preparation scan is implemented to produce a contrast-free MR-image of flowing fluid vessels.

14. Apparatus for acquiring a plurality of MR-images at respectively corresponding times related to a subject's cardiac cycle, said apparatus comprising an MRI system having at least one programmed computer configured to include:
   means for acquiring a first plurality of MR signals from a patient's tissue at respectively corresponding successive first time increments extending over a first time interval including a substantial majority of a subject's cardiac cycle;
   means for analyzing data representing magnitudes of the acquired first plurality of MR signals to define a second time interval, shorter than said first time interval, during the cardiac cycle whereat there is a relatively steep rise in signal magnitudes as a function of time corresponding with systole and diastole events of the cardiac cycle;
   means for acquiring a second plurality of MR signals from tissue of said patient at respectively corresponding successive second time increments during said second time interval, said second time increments being substantially shorter than said first time increments;
   means for generating image data representing at least one contrast-free image of flowing fluid vessels based on said second plurality of MR signals respectively acquired at different times during said second time interval; and
   means for outputting said generated image data to at least one of: (a) a display, (b) a non-transitory data storage medium, and (c) a remote device.

15. Apparatus as in claim 14, wherein said data representing magnitudes of the acquired first plurality of MR signals is displayed to an operator and an operator control input is accepted to define said second time interval based on such displayed data.

16. Apparatus as in claim 15, wherein said second time increment is automatically determined by the programmed computer based on said operator-defined time interval.

17. Apparatus as in claim 14, wherein said data representing magnitudes of the acquired first plurality of MR signals is automatically analyzed by said programmed computer and said second time interval is automatically defined by said programmed computer based on such data.

18. Apparatus as in claim 14, wherein said first time increments are on the order of 100 ms and said second time increments are on the order of 10 ms.

19. Apparatus as in claim 14, wherein said first time interval is triggered to begin by the occurrence of an R-peak in a QRS cardiac cycle.

20. Apparatus as in claim 14, wherein an image subtraction process is implemented to produce an image of flowing fluid vessels and the second time interval defines a time interval between systole and diastole of a cardiac cycle.

21. Apparatus as in claim 20, wherein successive difference images are generated between an MR-image acquired at systole and successive MR-images acquired at times approaching and/or at diastole.

22. Apparatus as in claim 21, wherein said successive difference images are displayed in cine mode to display flow-like hemodynamic images.

23. Apparatus as in claim 20, wherein said image of flowing fluid vessels is a 2D image.

24. Apparatus as in claim 20, wherein said image of flowing fluid vessels is a 3D image.

25. Apparatus as in claim 14, wherein a time-SLIP (spatial labeling inversion pulse) process is implemented to produce a contrast-free MR-image of flowing fluid vessels.

26. Apparatus as in claim 14, wherein a 2D BBTI (black-blood time to inversion) preparation scan is implemented to produce a contrast-free MR-image of flowing fluid vessels.

* * * * *